United States Patent
Feleppa et al.

(10) Patent No.: US 10,338,033 B2
(45) Date of Patent: Jul. 2, 2019

(54) TYPING AND IMAGING OF BIOLOGICAL AND NON-BIOLOGICAL MATERIALS USING QUANTITATIVE ULTRASOUND

(71) Applicants: Ernest J. Feleppa, Rye, NY (US); Jonathan Mamou, New York, NY (US); Daniel Rohrbach, Brooklyn, NY (US)

(72) Inventors: Ernest J. Feleppa, Rye, NY (US); Jonathan Mamou, New York, NY (US); Daniel Rohrbach, Brooklyn, NY (US)

(73) Assignee: Riverside Research Institute, New York, NY (US)

( * ) Notice: Subject to any disclaimer, the term of this patent is extended or adjusted under 35 U.S.C. 154(b) by 0 days.

(21) Appl. No.: 15/874,991

(22) Filed: Jan. 19, 2018

(65) Prior Publication Data
US 2018/0143166 A1 May 24, 2018

Related U.S. Application Data (63) Continuation-in-part of application No. 14/624,769, filed on Feb. 18, 2015, now abandoned.

(51) Int. Cl.
*G01N 29/12* (2006.01)
*G01N 29/032* (2006.01)
(Continued)

(52) U.S. Cl.
CPC ........... *G01N 29/12* (2013.01); *G01N 29/032* (2013.01); *G01N 29/449* (2013.01);
(Continued)

(58) Field of Classification Search
CPC .. G01N 29/12; G01N 29/4454; G01N 29/449; G01N 29/46; G01N 29/4472; G01N 2291/02466; G06F 17/18
(Continued)

(56) References Cited

U.S. PATENT DOCUMENTS 6,142,942 A * 11/2000 Clark .................. G01S 7/52025
600/443
6,238,342 B1 5/2001 Feleppa et al.
(Continued)

OTHER PUBLICATIONS

Saegusa-Beecroft, et al.,Three-Dimensional Quantitative Ultrasound for Detecting Lymph Node Metastases, 2013, pp. E1-E12, Journal of Surgical Research XXX (2013), Elsevier, USA.
(Continued)

*Primary Examiner* — Michael P Nghiem
*Assistant Examiner* — Dacthang P Ngo
(74) *Attorney, Agent, or Firm* — Keith D. Nowak; Danielle C. Sullivan; Carter Ledyard & Milburn LLP (57) ABSTRACT

An ultrasonic material-evaluation or classification method using spectral and envelope-statistics variables from backscattered ultrasound echo signals using an adaptive-bandwidth and combined with global variables. This classification method can be applied to any organ or tissue among biological materials and any non-biological material that produces backscattered signals as a result of microscopic internal in homogeneities such as a crystalline structure.

8 Claims, 8 Drawing Sheets
(5 of 8 Drawing Sheet(s) Filed in Color)

(51) Int. Cl.
*G01N 29/44* (2006.01)
*G01N 29/46* (2006.01)
*G06F 17/18* (2006.01)

(52) U.S. Cl.
CPC ..... *G01N 29/4454* (2013.01); *G01N 29/4472* (2013.01); *G01N 29/46* (2013.01); *G01N 2291/02466* (2013.01); *G06F 17/18* (2013.01)

(58) Field of Classification Search
USPC .......................................................... 702/56
See application file for complete search history.

(56) References Cited

U.S. PATENT DOCUMENTS

| | | | | |
|---|---|---|---|---|
| 2009/0078050 | A1* | 3/2009 | Sinha | G01N 29/036 73/632 |
| 2010/0063393 | A1* | 3/2010 | Moradi | A61B 8/0833 600/442 |
| 2015/0233811 | A1* | 8/2015 | Strohm | G01N 15/14 73/601 |
| 2016/0238568 | A1* | 8/2016 | Feleppa | A61B 8/08 |

OTHER PUBLICATIONS

Mamou et al., Three-Dimensional Quantitative Ultrasound to Guide Pathologists towards Metastatic Foci in Lymph Nodes, 2012, pp. 1114-1117, 34th Annual International Conference of the IEEE EMBS, USA.

Mamou et al., Three-Dimensional High-Frequency Backscatter and Envelope Quantification of Cancerous Human Lymph Nodes, 2011, pp. 345-357, Ultrasound in Med. & Biol., vol. 37, No. 3, Elsevier, USA.

Mamou, et al., Three-Dimensional High-Frequency Characterization of Cancerous Lymph Nodes, 2010, pp. 361-375, Ultrasound in Med. & Biol., vol. 36, No. 3, Elsevier, USA.

* cited by examiner

Fig. 7b

TYPING AND IMAGING OF BIOLOGICAL AND NON-BIOLOGICAL MATERIALS USING QUANTITATIVE ULTRASOUND

PRIORITY AND RELATED APPLICATION

This application is a Continuation in Part of U.S. patent application Ser. No. 14/624,769, filed Feb. 18, 2015, entitled "TYPING AND IMAGING OF BIOLOGICAL AND NON-BIOLOGICAL MATERIAL USING QUANTITATIVE ULTRASOUND," now abandoned, and is hereby incorporated by reference in its entirety.

U.S. Pat. No. 6,238,342 ('342 patent) is related to this application, and is hereby incorporated by reference in its entirety.

FIELD OF THE INVENTION

The present invention relates to improved typing and imaging of biological and non-biological materials by combining quantitative-ultrasound (QUS) estimates based on the statistics of the envelope of echo signals generated using pulse-echo ultrasound with QUS estimates based on the normalized power spectra of echo signals generated using pulse-echo ultrasound and global variables associated with the material of interest.

BACKGROUND OF THE INVENTION

The improvements described herein generalize the definition of QUS by adding:

(1) estimates based on variables of the statistics of the envelope of linearly amplified, radio-frequency ultrasound echo signals backscattered from biological or non-biological materials to (2) estimates based on variables of normalized power spectra of linearly amplified, radio-frequency ultrasound echo signals in previously described QUS methods such as those shown in the '342 patent, and optionally (3) one or more global variables such as clinical data, e.g., antigen level or patient age, when typing tissue or such as material properties, e.g., acoustic attenuation or mass density, when typing non-biological material.

The improvements also generalize the application of the covered QUS methods to any and all materials in which pulse-echo ultrasound produces echo signals within the material and where such echo signals result from spatial variations in the acoustical impedance of the material on a scale of fractions to multiples of the incident acoustical-pulse wavelength.

Although specific clinical examples are cited herein to illustrate applications of the described method, the method is applicable to a very broad range of material-typing and imaging applications in addition to the cited clinical, tissue-typing and imaging applications. Examples of potential non-biological material-typing and imaging applications include, but are not limited to, assessment of composite quality, fiber density in fiber-reinforced plastics, crystalline-material properties, particle size and concentration in liquid suspensions, etc. An example of a potential non-clinical, biological-material typing and imaging includes, but is not limited to, beef-quality grading. Examples of potential clinical applications include, but are not limited to, distinguishing among healing, non-healing and infected wounds; distinguishing between ischemic and non-ischemic myocardium; distinguishing among progressing, static, and regressing lesions; distinguishing between lesions that are responsive to treatment and those that are unresponsive to treatment; etc. Furthermore, in clinical applications, the method may be able to grade conditions such as, for example, the degree of treatment response, severity of ischemia, extent of infection, rate of healing, depth of burns, pressure or friction-ulcer status, progression of disease; etc.

For example, two salient, representative clinical applications are detection and imaging of cancer in the prostate gland or of metastases in lymph nodes. Reliable detection of primary-cancer foci in the prostate or metastatic foci in lymph nodes is critical for staging the disease and planning its treatment. The described method of cancer detection analyzes raw ultrasound echo-signal data in two- or three-dimensions (2D or 3D) in combination with global clinical variables such as serum PSA (prostate-specific antigen) values in the case of prostate cancer or primary-tumor type in the case of lymph-node metastases to generate 3D images that depict cancerous foci in the prostate or lymph nodes and thereby that reliably detect, characterize, and localize metastatic regions.

A reliable method using spectrum-analysis-based QUS to characterize and type biological tissue is described in the '342 patent and is incorporated herein by reference. The '342 patent describes a method that combines spectrum-analysis-based QUS variables (i.e., the slope, intercept, mid-band variables of the so-called normalized power spectrum and also the effective scatterer size and so-called acoustic concentration estimates that are derived from the spectral variables and known ultrasound-system properties) with global clinical data.

The improvements described herein additionally combine variable values of the envelope statistics of ultrasound echo signals derived from the tissue of interest with the spectrum-analysis-based variable values and global variables described in the '342 patent, and/or described herein.

SUMMARY OF THE INVENTION

Quantitative ultrasound (QUS) is generalized to add estimates derived from the statistics of envelope detected echo-signal data, to estimates based on variables of the normalized power spectra of echo signals generated by pulse-echo ultrasound in 2D or 3D, combined with the values of global variables of the biological or non-biological material to characterize said biological or non-biological material based on its properties at microscopic levels on a scale that ranges from a fraction to a small multiple of the wavelength of the incident ultrasound pulse. Variables of the normalized power spectrum are computed from acquired, linearly amplified, radio-frequency echo signals backscattered from the material being evaluated. Variables also are derived by computing variables of the statistics of the envelope of the back-scattered signals. The statistics of the envelope of the echo signal are modeled using distributions such as, but not limited to, Nakagami and homodyned-K distributions.

A significant improvement in the accuracy of the QUS results generated by the initial invention is achieved by a unique method of adapting the bandwidth over which spectral content is computed to provide the QUS results. The bandwidth used is based on the signal-to-noise ratio (SNR), which is defined as the difference between the spectral peak amplitude and the noise level. The noise level is approximately constant and depends on the instruments used and other, e.g. ambient, sources of unwanted signals, etc. More specifically, as described below, a higher SNR allows data to be analyzed over a larger bandwidth while a lower SNR limits data analysis to a smaller bandwidth. This feature ensures that data analysis is limited to the signal derived from the tissue or non-biological material of interest, i.e., only utilizes information useful for characterizing tissue or non-biological material while eliminating information corrupted by noise. The application of adaptive-bandwidth methods is beneficial in the typical situation in which attenuation causes the SNR to decrease as ultrasound echo signals are obtained from greater depths in the tissue or non-biological material of interest. (Attenuation is due to scattering and absorption of ultrasound. Scattering is caused by microscopic variations, or inhomogeneities, in acoustic impedance.) The combined set of spectral and statistics-based variables, computed using an adaptive-bandwidth approach, increases the accuracy of the QUS parameter estimates of the described improvements to the '342 patent. Once computation of QUS estimates derived from the spectra over the appropriate bandwidth and from statistics-based variables is complete, the estimate values can be combined further with one or more global variables associated with the material being evaluated for the purpose of classifying, grading, or otherwise characterizing the material using linear or non-linear classification methods such as, but not limited to, linear-discriminant methods, artificial neural networks, nearest-neighbor algorithms, and support-vector machines. Subsequently, color-coded QUS-based images can be constructed from either QUS values or from classification values derived from them on a pixel-by-pixel basis to produce 2D depictions or on a voxel-by-voxel basis to produce 3D depictions to visualize, for example, an entire lymph node or a volume of a fiber-reinforced plastic.

The invention employs in part an ultrasound apparatus for performing material classification as disclosed in the '342 patent which is incorporated herein by reference. Such an apparatus includes a so-called pulse-echo ultrasound scanner for acquiring original, so-called radio-frequency or "RF" echo signals, backscattered by the material being tested, such as biological tissue or non-biological material, such as fiber-reinforced plastic. Analog RF echo signals are presented to a digitizer that converts the RF signals to digital signals, representing a plurality of spatial points in a scanned plane. A digital processor operatively computes so-called normalized power spectra and adaptive bandwidth from the digital signals provided by the digitizer and extracts spectral variables that characterize the original RF signals. Concurrently, the processor computes the envelope of the RF signals and, from the computed envelope, it computes the associated statistics of the envelope. An input device is also included for providing the values of global variables to the processor. Alternatively, global variable values may be computed directly from the ultrasound data, e.g., specimen shape factors, specimen volume, etc. A classifier that is responsive to at least a portion of the set of spectral variables, at least a portion of the set of envelope statistics, and at least a portion of the set of global variables, is employed to assign a material-classification score to the spatial points of the plane or volume covered by the ultrasound scan. A display may be provided for displaying the assigned classification scores in a color- or gray-scale encoded manner in a 2D or 3D image, but a display is not required to practice the invention described herein.

BRIEF DESCRIPTION OF THE DRAWINGS

The patent or application filed contains at least one drawing executed in color. Copies of this patent or patent application publication with color drawings) will be provided by the Office upon request and payment of the necessary fee.

Further objects, features and advantages of the invention will become apparent from the following detailed description taken in conjunction with the accompanying figures showing illustrative embodiments of the invention, in which:

FIGS. 4a and 4b show an example of analysis regions applied at different depths to data in which the SNR and bandwidth are less in FIG. 4b than in FIG. 4a;

FIGS. 6a and 6b provide a graph showing an example of a reference spectrum, an un-normalized signal spectrum in FIG. 6a, and a difference, i.e. normalized, signal spectrum in FIG. 6b from the shallow region of interest depicted in FIG. 4a;

DETAILED DESCRIPTION OF THE INVENTION

Figure 1:
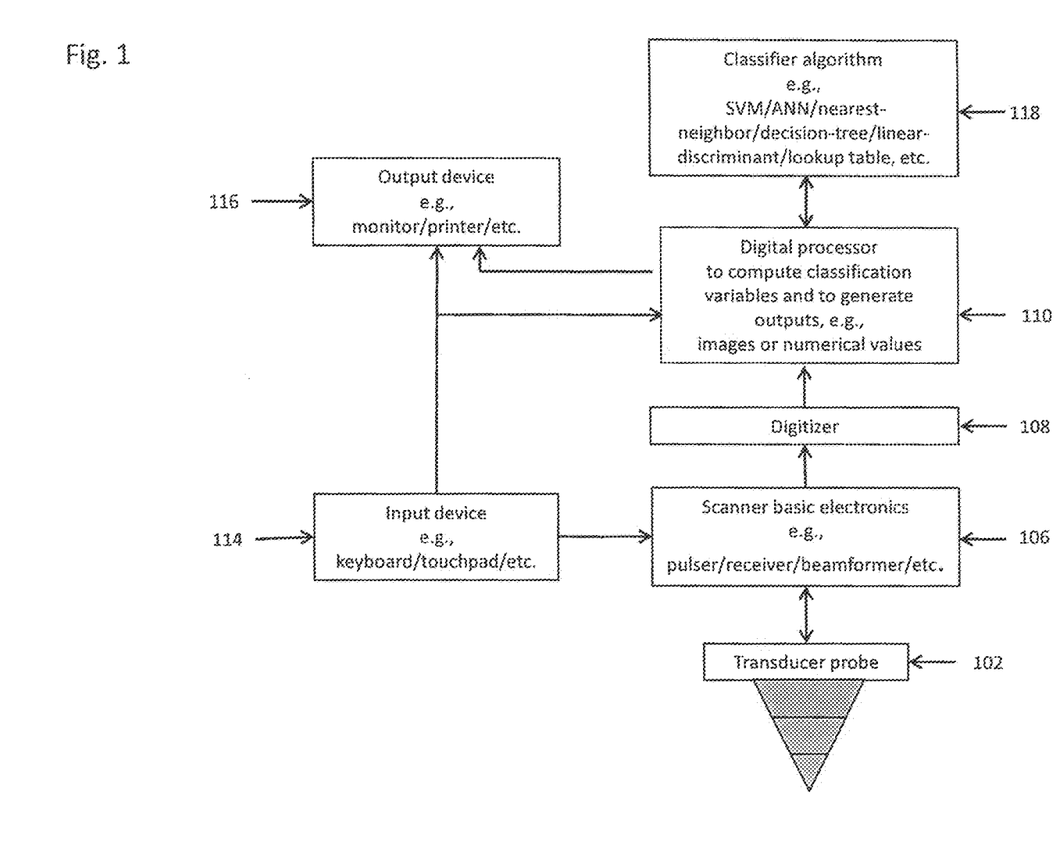
FIG. 1 is a block diagram of an ultrasound imaging system formed in accordance with the present invention.

FIG. 1 is a general block diagram of system hardware that could be used in conjunction with the present invention. The general system hardware includes an ultrasonic transducer probe 102 operatively coupled to an ultrasound scanner 106. The signals from the scanner 106 are converted from an analog RF signal to a digital signal by a digitizer 108 operating under the control of a processor 110. In an exemplary embodiment, the digitizer 108 operates at a 50 MHz sampling rate to acquire, for example, 2500, 8-bit samples of echo-signal data in a frequency band extending from 3.5 to 8.0 MHz along each of 318 scan lines in a 112-degree scanning sector. A small set of these sample points represents a pixel in an ultrasound image. This results in a sector with a radius of about 3.6 cm. The digital samples are stored in a computer memory under the control of processor 110.

The processor 110 may be included in a desktop computer or workstation interfaced with the scanner 106 or may be integral to the scanner 106. A high-speed processor is required for real-time imaging. In a laboratory setting, the digitizer 108 can take the form of digital sampling oscilloscope. However, for commercially produced clinical or material-testing scanners, the digitizer 108 will generally be integrated into the scanner 106 or will be integrated with a subsystem along with processor 110. Optionally, the digitizer 108 and associated interface circuitry to a conventional ultrasound scanner 106 can be provided on a computer interface card for a conventional desktop computer system or workstation in which the processor 110 resides.

The system of FIG. 1 also includes an input device 114 for manually entering data into the system 100. The input device may take the form of a keyboard, touch screen, or digital pointing device, such as a computer mouse, used in conjunction with a display device 116. The display device 116 can be a standard computer monitor or printer.

A critically important element of the present invention is a classifier 118. The classifier 118, which may be implemented as a look-up table, trained neural network, nearest neighbor model, support-vector machine, and the like, is developed or trained using conclusive material-property data variables (e.g., histological data from biopsy results or known reinforced-plastic material properties) with matching RF-signal spectral-variable values, envelope-signal statistics-variable values, and global-variable values 110.

Figure 2:
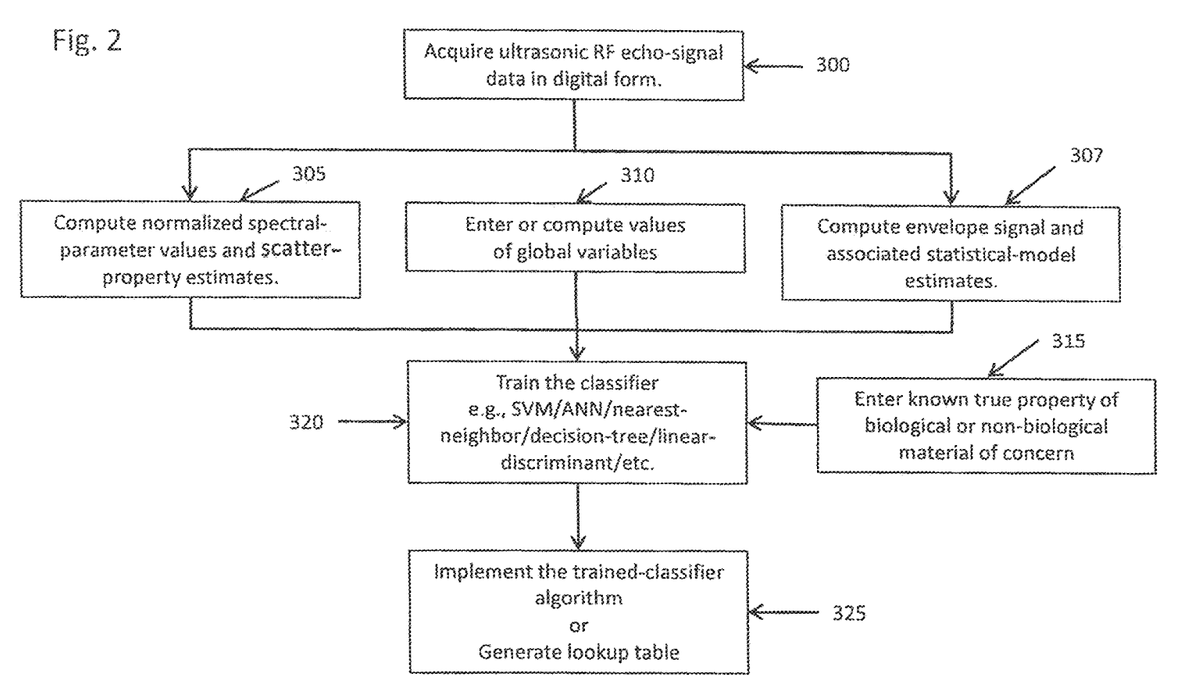
FIG. 2 is a flow chart depicting the process of training a classifier and optionally generating a derivative thereof, such as a look-up table, for performing tissue classification in accordance with the present invention.

FIG. 2 is a flow chart illustrating exemplary steps used to develop and train the classifier 118. Preferably, the classifier 118 takes the form of a "trained" non-linear classifier, such as a support-vector machine, but other linear and non-linear classifiers also can be employed. In order to develop a "trained" non-linear classifier 118, training data are required. These training data must include a sufficiently large number of independent records to provide adequate statistical stability; each record includes spectral- and statistical-variable values computed from the RF echo-signal data (steps 300, 305 and 307), global-variable values, for instance known reinforced-plastic material properties (such as mass density) or clinical data (such as patients' age, ethnicity, prior medical history, or, in the case of prostate-cancer detection, PSA level) (step 310) and corresponding "gold-standard" data (step 315), for instance, the clinical "gold standard" histologically established tissue properties (such as biopsy results) for each record. The set of spectral-parameter values and envelope-statistics-parameter values are matched with gold-standard data (such as histological determinations of the actual tissue in the biopsy sample or independently measured actual fiber content in a reinforced-plastic).

The classifier is trained in step 320 and the trained-classifier algorithm is implemented in step 325. Various algorithms for classifiers are known and will not be further described herein.

After the RF backscatter data are acquired (step 300), digital signal analysis is performed on the acquired data to compute the set of QUS estimates consisting of spectral and envelope-statistics variable values representing the data (steps 305 and 307). In the '342 patent, spectral variables that have been found to be of interest in cancer diagnostics include the slope, intercept and mid-band values of a linear regression approximation to the normalized power spectrum of the backscattered radiofrequency (RF) echo signals. Scatter-property estimates, such as the effective scatterer size and so-called acoustic concentration derived from the spectral variables and known ultrasound-system properties, also have proven to be of value in classifying tissue. These estimates are computed from the echo signals in a user-specified analysis region of interest (ROI). Four additional variables have been shown to improve classification; these are derived by fitting envelope-amplitude distribution models to the envelope statistics of the backscattered envelope signals statistics based on the Nakagami and homodyned-K statistical models (step 307). The four new QUS variables associated with these two models are α, Q, k and μ. However, other statistical models and associated variables can be used. The method is not limited to these statistical models.

To compute the variables for training the classifier, a user-specified ROI is applied to the acquired RF data to select a set of samples of the RF signals that spatially corresponds to the region from which the gold-standard determination is made, for instance the tissue region exactly matching the tissue sampled by the biopsy procedure or the portion of the reinforced plastic that will be exposed for fiber-density determination. The calculation of the spectral variables from RF echo-signal data defined in the '342 patent has been widely publicized and is a technique that is well known in the art of ultrasound diagnostics. The statistics of envelope-detected echo signals are quantified using Nakagami and homodyned-K or other applicable statistical models. For instance, envelope-statistics variables, α, and Q, are obtained by fitting a Nakagami probability density function to that of the envelope of RF data within the ROI, while the variables, k and μ, are obtained by fitting the homodyned-K probability density function to that of the envelope of RF data within the ROI.

Tissue classification using spectral and derived variables, envelope statistics from ultrasound echo signals combined with global-variable values is an approach that can be generalized for application to any organ or tissue and also to a wide variety of non-biological materials. In clinical applications, the approach can be used to monitor therapy or disease progression, and can be applied to diffuse disease, healing processes, etc., and is not limited to cancer applications. Examples of analysis using the present invention in clinical applications are provided below.

Figure 3:
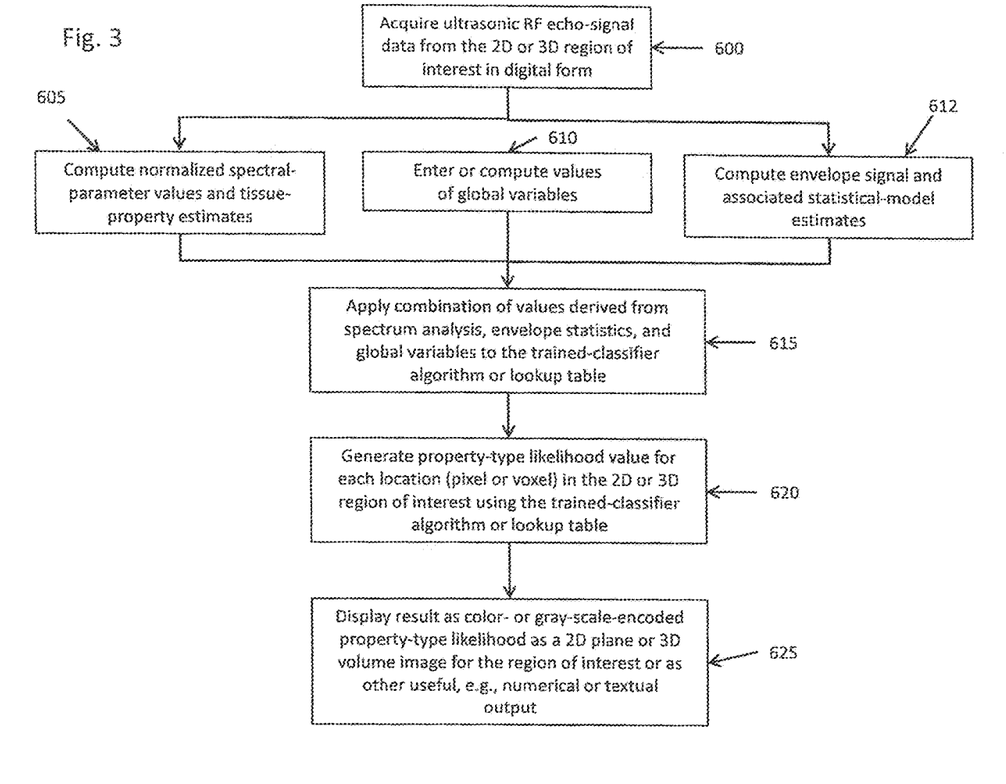
FIG. 3 is a flow chart depicting the process of generating images using computed spectral estimates, statistical estimates, global-variable values, and a classifier or a derivative thereof, such as a look-up table, to distinguish the material being evaluated into a number of classifications, such as most-likely tissue type or levels of suspicion of cancer.

FIG. 3 is a flow chart illustrating an exemplary clinical application of the present invention. Global variables such as clinical data or non-biological data are input to the system (step 610) by a person using the input device 114. RF echo-signal data are acquired and digitized (step 600). Spectral-variables and scatterer-property values along with variables of the envelope statistics comprising the full set of QUS-variable values are extracted and computed (steps 605 and 612). The selected global-variable and QUS-variable values are applied as input variables to the classifier 118, then normalized to the input range of the classifier 118 on a pixel by pixel basis, such that each pixel of the sampled ultrasonic scan is assigned a classifier-score value (step 615). For real-time operation, the classifier 118 can take the form of a look-up table whose values are derived from a trained linear or non-linear classifier. Alternatively, if the processor 110 is sufficiently powerful, the classifier 118 may omit the look-up table and the classifier-score value can be assigned for each pixel by applying the input variable values to the optimal classifier and computing classifier-score values directly using the trained classifier.

In step 620, the property-type likelihood value for each location (pixel or voxel) in the 2D or 3D ROI is generated using the trained-classifier algorithm or look-up table. In step 625, a display is generated that can be color or gray scale-encoded, property-type likelihood result. The display can be a 2D plane or a 3D volume for the ROI, or as any other useful output.

Although evaluating the classifier scores over a broad range of values is important to account for a possibly large number of variables involved in the process, the display need not show each individual classifier-score value as a unique display variable. The range of classifier-score values can be grouped into a plurality of ranges that correspond to most-likely material categories, for example, most-likely tissue types, a number of levels of suspicion (LOS) for cancer in a clinical application or similar categories for non-biological material. Each of the LOS ranges is assigned a unique image characteristic, such as a color or grey scale value, for pixels within that range for displaying the results (step 625).

Although the present invention has been partially described in connection with lymph nodes, the present techniques are generally applicable to any region of a body where ultrasound backscattered echo signals can be obtained and also are applicable to non-clinical applications, e.g., those involving research with experimental animals, and to evaluations of non-biological materials. Each specific material type requires its own classifier 118 appropriately trained using a suitable database of global-variable values, QUS variable values (spectral and envelope statistical), and gold-standard results for the target application.

In clinical applications, in addition to classifying tissue in accordance with a level of suspicion or likelihood for cancer, various other tissue types or changes in tissue characteristics can be evaluated with the present invention. For example, changes in tissue in response to therapy, disease progression, injury severity, injury healing, and the like can be assessed. In practice, a clinical device will have a menu of applications to select from as part of the initial instrument set up.

In non-clinical biological applications, for example those involving experimental animals, various other tissue types or changes in tissue characteristics can be evaluated with the present invention. For example, as in clinical applications, changes in tissue in response to therapy, disease progression, injury severity, injury healing, and the like can be assessed quantitatively by assessing classifier-score values. In practice, a device for non-clinical, biological use will have a menu of applications to select from as part of the initial instrument set up.

In non-biological, materials-evaluation applications, in addition to classifying material properties, changes in material characteristics can be evaluated with the present invention. For example, changes in composite integrity or alterations in crystalline structure over time may be sensed and depicted quantitatively. In practice, a device for non-biological, material-evaluation use will have a menu of applications to select from as part of the initial instrument set up. The use of the present invention is demonstrated in the following examples.

EXAMPLE 1

In this example, 110 axillary lymph nodes dissected from breast-cancer patients were analyzed. Of these nodes, 17 were cancerous and 93 non-cancerous. Analysis results for the 110 axillary lymph nodes are presented in Table 1 with scan volume being the global variable for this example.

TABLE 1

| Variables | ROC AUC |
|---|---|
| Spectral variables | 0.706 +/ 0.070 |
| Spectral variables + scan volume | 0.725 +/− 0.070 |
| Spectral variables + scan volume + envelope statistics | 0.877 +/− 0.048 |

In this example, using only QUS-variable values derived from spectrum analysis resulted in an ROC AUC value of 0.706+/0.070. ROC AUC values provide a measure of classifier performance in which an AUC value of 0.5 indicates entirely random classification and an AUC value of 1.0 indicates perfect, error-free classification. Adding the global variable of scan volume to the analysis improved the performance to an ROC AUC value of 0.725+/−0.070. Finally, adding envelope statistics to the analysis further improved the performance to an ROC AUC value of 0.877+/−0.048. A comparison of ROC AUC values for spectral variables to the corresponding AUC values for spectral variables with envelope statistics and a global variable value shows a significant improvement in identification of cancerous nodes.

EXAMPLE 2

In another example, 289 dissected lymph nodes of mixed primary-cancer types were analyzed. Of these nodes, 43 were histologically proven to be positive and 246 were proven to be negative for cancer. The mixed nodes included 110 breast-cancer nodes with 17 proven to be positive and 93 proven to be negative plus 179 colorectal-cancer nodes with 26 proven to be positive and 153 proven to be negative for cancer. Table 2a shows results obtained with a non-linear classifier—a support-vector machine (SVM)—while Table 2b shows results for a linear classifier—linear discriminant analysis (LDA). The variables investigated include a QUS variable derived from spectrum analysis, a QUS variable derived from envelope statistics and two distinct global variables: primary cancer type and scan volume (proportional to lymph-node volume). The non-linear analysis (Table 2a) shows that adding global variables significantly improves classifier performance over the spectral variable alone. Similarly, adding the envelope-statistics further improves the performance. Table 2b shows the same improvement trend when global and envelope-statistics variables are added. Finally, comparing Tables 2a and 2b demonstrates how non-linear classification methods can perform better than linear methods.

TABLE 2a

SVM-based Classification

| Variables | ROC AUC |
|---|---|
| Spectral variables | 0.66 +/− 0.04 |
| Spectral variables + primary cancer type | 0.71 +/− 0.04 |
| Spectral variables + primary cancer type + scan volume | 0.79 +/− 0.03 |
| Spectral variables + primary cancer type + scan volume + envelope statistics variables | 0.87 +/− 0.02 |

TABLE 2b

Linear-discriminant-based Classification

| Variables | ROC AUC |
|---|---|
| Spectral variables | 0.70 +/− 0.04 |
| Spectral variables + primary cancer type | 0.68 +/− 0.04 |
| Spectral variables + primary cancer type + scan volume | 0.78 +/− 0.03 |

TABLE 2b-continued

Linear-discriminant-based Classification

| Variables | ROC AUC |
|---|---|
| Spectral variables + primary cancer type + scan volume + envelope statistics variables | 0.78 +/- 0.03 |

EXAMPLE 3

Non-Biological Material

To demonstrate how the invention can be used to type non-biological materials, radio-frequency ultrasound data was collected from two phantoms (PA and PB) using a single-element transducer operating at 10 MHz. The data were processed to yield two QUS-variable estimates associated with the backscattered spectrum (i.e., spectral intercept and spectral slope) and two additional QUS variables associated with the Nakagami envelope statistics model. In both cases, correction was made for the different attenuation of the two phantoms. The optional global variable was not used for this example. Table 3 summarizes the ability of these variables to distinguish between PA and PB.

TABLE 3

| Variables | ROC AUC |
|---|---|
| QUS Spectrum | 0.75 |
| QUS Spectrum + Envelope | 0.95 |

The results demonstrate that the envelope variables significantly increase classification performance over spectral variables alone.

In order to improve QUS-parameter estimation, the frequency band over which the models are fit may be varied for each ROI based on the signal-to-noise ratio (SNR) in the ROI. An algorithm is used to apply wider bandwidths to ROIs with higher SNR values. In the present invention, the overall frequency band to be considered is determined and then the portion of the overall band that is from relevant backscatter signal is determined. A noise plateau (NP, in dB) is defined as the average magnitude of the power spectrum in a specified frequency band outside the band comprising the relevant backscatter signal.

A critical element necessary for improved classification performance is the use of an adaptive bandwidth based on the SNR of each ROI, rather than a fixed bandwidth used in prior art. The reason for using an adaptive bandwidth is to obtain the best possible estimate, using a larger bandwidth when a better SNR exists, because it increases the precision of the QUS estimates, and using a smaller bandwidth when a poorer SNR exists, in order to reject noisy data, which will also increase the precision of the QUS estimates.

The refinement of the adaptive-bandwidth settings based on the signals SNR improves results. For example, implementation of automated SNR-detection algorithms may improve overall classification performance. Using an adaptive bandwidth, rather than using a fixed bandwidth provides superior classification performance compared to classification performance obtained using the conventional fixed bandwidth. The adaptive-bandwidth method optimizes the bandwidth for the available signal no matter what causes the variation in backscatter-signal and related spectral amplitude. Attenuation is an example as one cause for signal reduction; however several factors affect signal and spectral amplitudes such as scatterer size, scatterer concentration, scatterer mechanical properties compared to those of their surroundings, beam diffraction and focusing effects, and reflections in intervening tissue, etc. The signal amplitude can go down if scattering weakens for example, because scatterers become smaller, their concentration decreases, or they become more like their surroundings. Except for attenuation in a uniform material, signal and spectral amplitudes may increase with depth, amplitude does not necessarily always decrease with depth. Signal amplitude can increase, for example, if scatterer size increases or scatterer concentration increases, etc.

The energy in an ultrasound echo signal spans a range of frequencies with a bell-shaped distribution of signal power vs. frequency. Noise however, is also always present to some degree in echo signals and typically has an approximately flat distribution of power vs. frequency. Therefore the overall distribution of power vs. frequency is level from the noise alone at high and low frequencies and a bell-shaped curve in the middle over the frequency range where the echo-signal amplitude exceeds the noise amplitude. If the echo signal decreases in amplitude, the signal-spectrum curve drops into the noise spectrum, essentially without changing shape. Therefore, the width of the signal part of the spectrum decreases as it sinks into the noise. Such sinking occurs with depth into the target, e.g., tissue, because of attenuation, for example. (As previously mentioned depth-dependent attenuation is one example of a cause for signal and spectral amplitude reduction with depth. The adaptive-bandwidth method optimizes the bandwidth for the available signal no matter what causes variations in backscattered-signal and spectral amplitudes.) Also, because of the frequency dependence of attenuation in most materials, e.g., tissue, the high-frequency portion of the bell-shaped curve decreases faster with depth into the target than the lower-frequency part. So the bell-shaped curve effectively shifts toward lower frequencies as it sinks because of attenuation. For example, attenuation causes high frequencies to fall off faster with depth than low frequencies, so that a shift in the spectral peak toward lower frequencies occurs. For the adaptive-bandwidth method, this means that the bandwidth contracts more rapidly with depth at high frequencies than at low frequencies, i.e., the maximal usable frequency in the signal spectrum decreases more rapidly with depth than the minimal frequency increases. Therefore, bandwidth does not "shrink" symmetrically as attenuation of the signal increases with depth into the target material. Attenuation is frequency dependent and the dependence depends on the type of material. In tissue, for example, attenuation is approximately a linear function of frequency. So, if the frequency is doubled, then the signal losses due to attenuation are doubled and signal amplitude is halved. In pure water, for example, attenuation is lower than in tissue, but it increases approximately as the square of the frequency. So when the frequency is doubled, the signal losses due to attenuation are quadrupled. Therefore the adaptive-bandwidth method of the present invention decreases the high-frequency limit on the usable band more rapidly than it increases the low-frequency limit as signals come from deeper in the target material. In effect, the spectrum gets pushed down into the noise and also pushed to the "left," toward lower frequencies, as attenuation decreases the backscattered-signal amplitude with depth. Adapting the bandwidth used for QUS computations are performed takes into account these bandwidth-altering effects and assures that QUS results are derived from signal spectra—not from noise.

Maximal improvements over the prior art, including improvements in sensitivity (SEN) and specificity (SPE), occur when using the present invention (statistics parameters+global variables+spectrum-derived features). Sensitivity is the fraction of actually positive cases that are correctly identified as positive cases. Specificity is the fraction of actually negative cases that are correctly identified as negative cases.

EXAMPLE 4

Figure 4A:
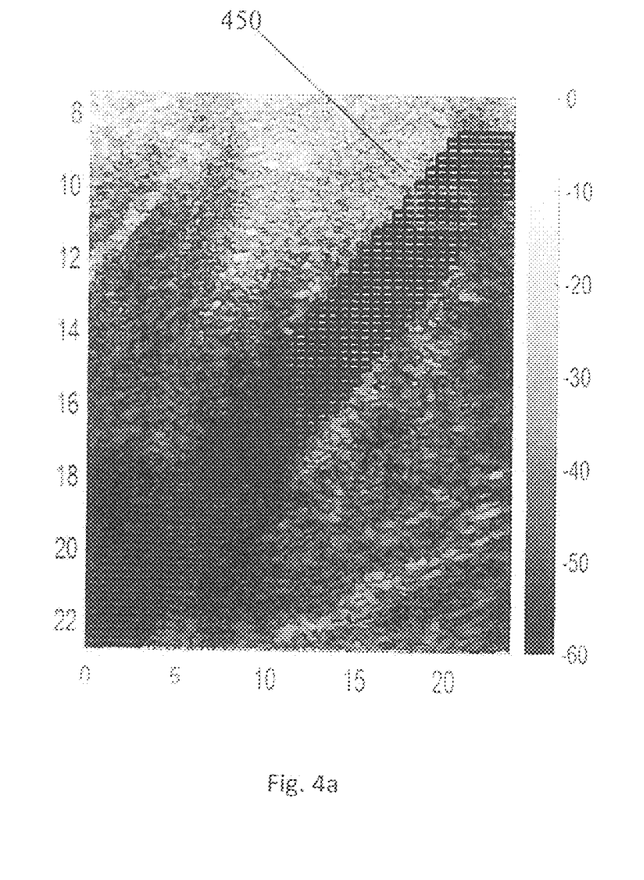
Figure 4B:
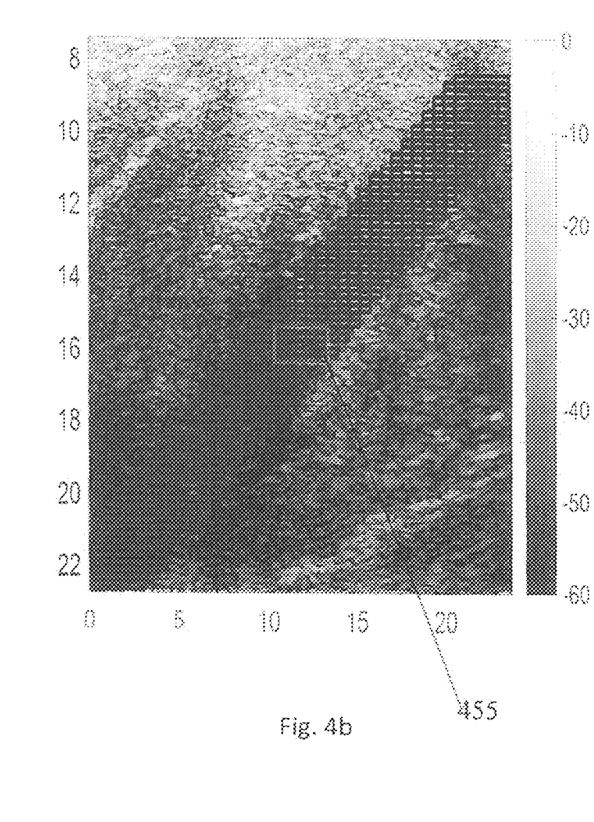

FIGS. 4a and 4b show an example of results derived from data acquired in a study of prostate-gland characterization and prostate-cancer detection undertaken collaboratively with Exact Imaging, Inc. FIG. 4a shows an ROI, red rectangle 450, that is closer to the surface and suffers less attenuation than is suffered by the deeper ROI, red rectangle 455, in FIG. 4b.

Figure 5:
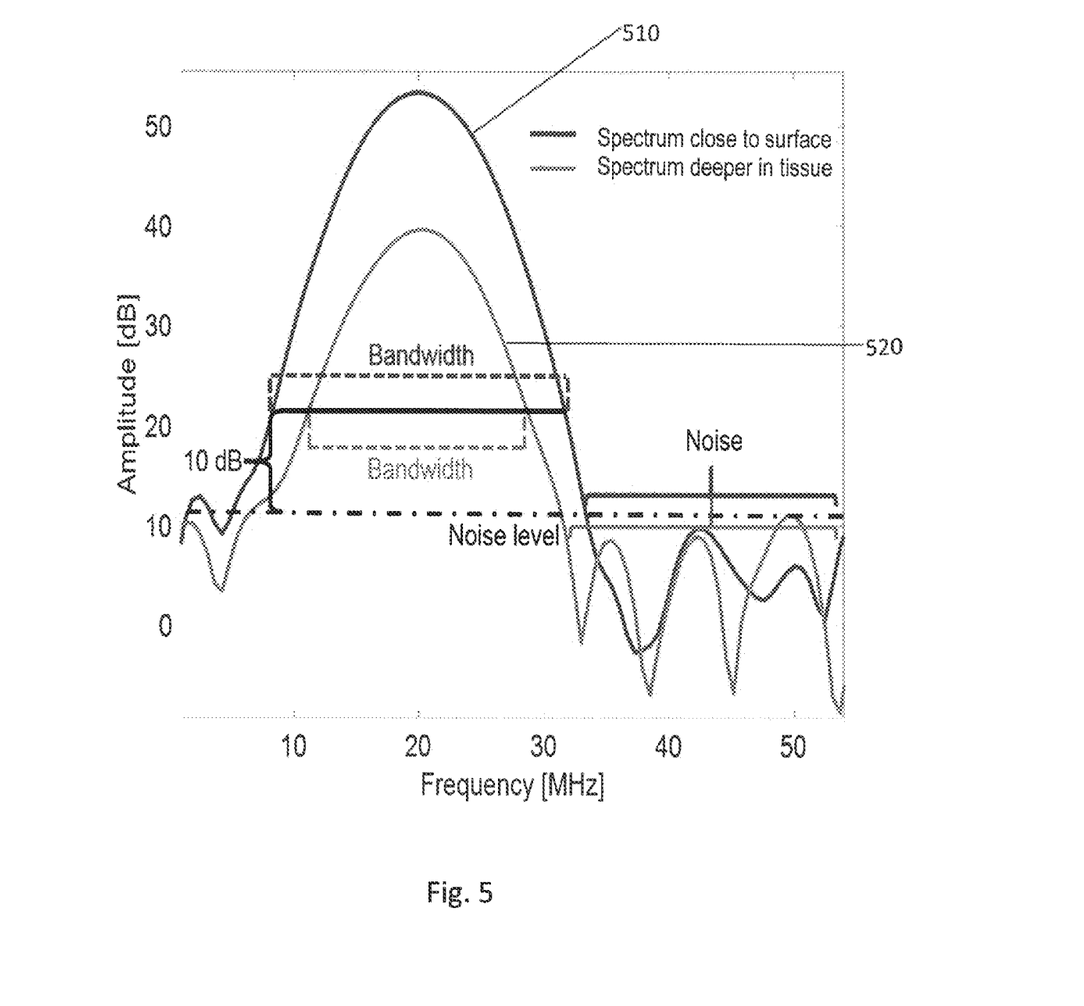
FIG. 5 provides a graph showing a principle approach of the present invention.

FIG. 5 shows a principle approach of the present invention. Because of attenuation, the spectral amplitude, or spectral signal-to-noise ratio (SNR) of the power spectrum derived from stronger signals originating from tissues closer to the surface 510 is larger than the SNR of the power spectrum derived from signals originating from deeper tissue regions 520. The SNR is defined as the difference between the spectral peak amplitude at ~22 MHz in FIG. 5 and the noise level. The noise level is approximately constant and depends on the instrument and other ambient sources of unwanted signals.

Information that is useful for characterizing tissues or non-biological materials is contained only in the noise-free portion of the spectrum. The noise-free frequency range of the spectrum defines its useful bandwidth. As illustrated in FIG. 5, the useful bandwidth is larger for the spectrum derived from the signals that originate closer to the sample surface than for the spectrum derived from the deeper signals.

The spectral content within the bandwidth contains the tissue-property-relevant information. To optimize the bandwidth (i.e. to utilize the largest noise-free bandwidth) for each individual spectrum, the present invention provides an adaptive-bandwidth method. The method consists of first detecting the noise level and then detecting the spectral frequency that occurs at 10 dB above the noise level. (The 10 dB margin is used as an example in the present invention. Different applications and different shapes in the noise spectra may call for different margins. A very flat noise spectrum might allow a smaller margin, for example. A need to maximize bandwidth also might call for a smaller margin. A very irregularly shaped noise spectrum or one that varies in time may call for a larger margin. The margin can be set to give the best (widest) practical bandwidth in any given application; based on what provides the best results in the particular application in which the frequency margin is applied.)

The conventional method defines a fixed bandwidth in which the signal spectra are analyzed. To guarantee noise-free spectra with conventional methods, a fixed bandwidth is determined by the spectrum with the lowest SNR. If the frequency boundaries are too large, for example 10 MHz to 32 MHz in FIG. 5, the noise will be included in the spectral analysis for signals with smaller SNR, 520. However, if the frequency boundaries are too small, the valuable information in signals with a large SNR will be lost.

Figure 6A:
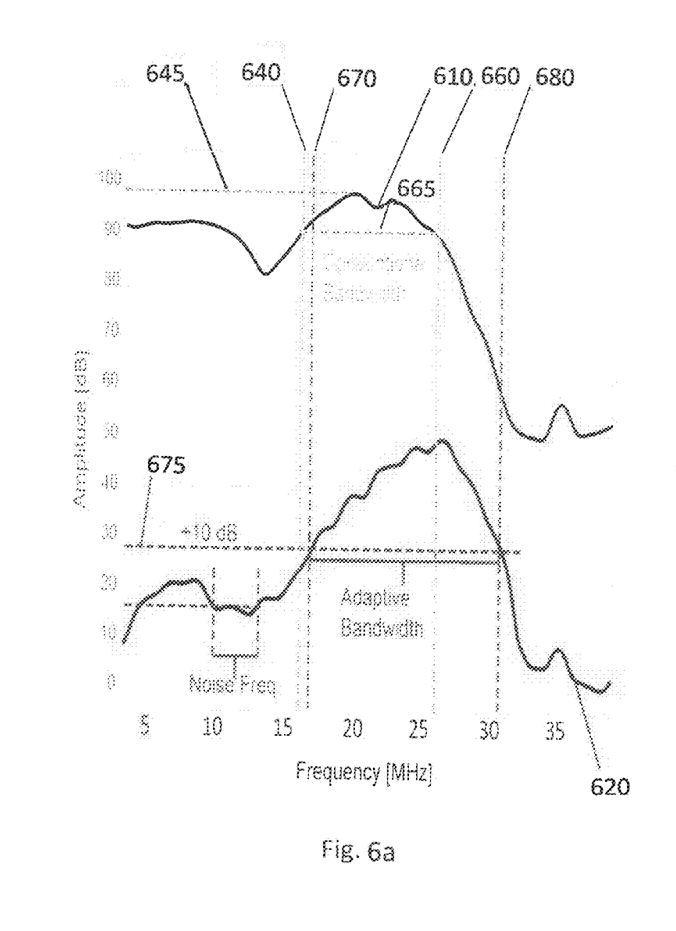
Figure 6B:
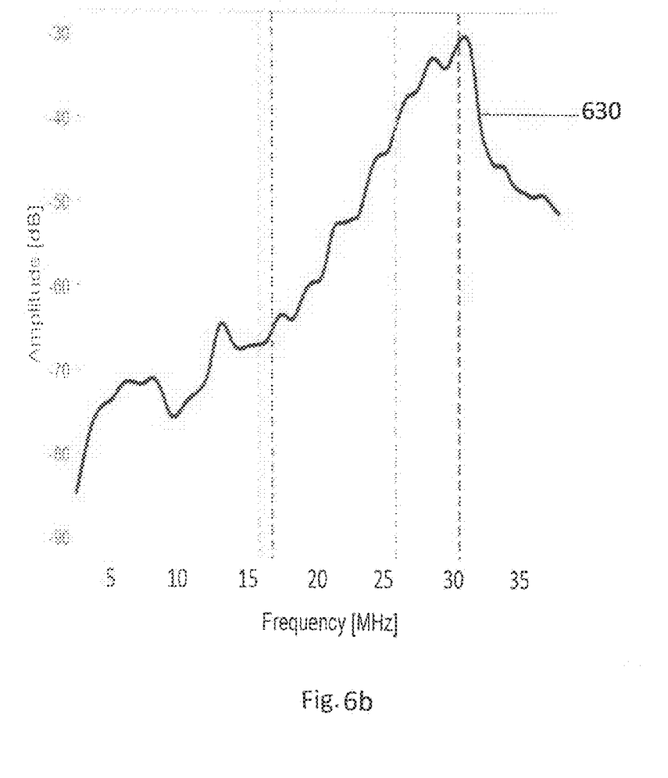

FIGS. 6a and 6b show an example of a reference spectrum 610, signal spectrum 620, and difference spectrum 630. The sample spectrum was obtained from the ROI, 450 in FIG. 4a. In the present example, NP is the average spectral amplitude in the frequency range from 10 to 12 MHz. The bandwidth and frequency boundaries (i.e. the low and high cutoff frequencies) were then estimated at NP+10 dB. A minimal bandwidth for use in classification may be defined; when this minimum is reached, QUS processing does not occur because QUS estimates would be considered to be unreliable at such narrow bandwidth. In the present example, ROIs with a bandwidth of less than 15 MHz are precluded from QUS processing.

Estimation of parameters, such as spectral slope, i.e. the slope of a linear-regression line fit to the normalized power spectrum, is performed over the bandwidth in which the signal spectrum exceeds the noise spectrum by a specified amount, e.g., by 10 dB in the present examples. Spectral content outside the noise-free bandwidth is derived only from instrument and ambient noise and does not contain information about the sample, such as tissue. Using the largest possible noise-free bandwidth yields the most-reliable and most-stable QUS estimates.

Conventional methods for estimating the bandwidth typically employ a fixed frequency range that corresponds to the two (low- and high-frequency) −6 dB (i.e., 6 dB below the maximal spectral amplitude) points of the reference spectrum. FIG. 6a illustrates the conventional method of estimating the bandwidth between −6 dB points on the reference spectrum, with the gray dotted lines 640, 645, 660, 665. For comparison, the blue dotted lines of FIG. 6a, 670, 675, 680, illustrate the new adaptive-bandwidth method. In a noise region, e.g., between 10 and 12 MHz, the noise level is determined. Then the two, low- and high-frequency, +10 dB (above noise) points on the sample spectrum determine the "adapted" bandwidth of the sample spectrum. The example illustrates how the bandwidth is improved (made wider) for a strong signal when using the adaptive-bandwidth settings. (The possibility exists that the amplitudes of the noise spectra at the high-frequency and low-frequency edges of the signal spectrum are different. So, even if the same margin (e.g., 10 dB) is used at high and low frequencies, the margins at high and low frequencies can be based on different noise-spectrum amplitudes.)

Figure 7A:
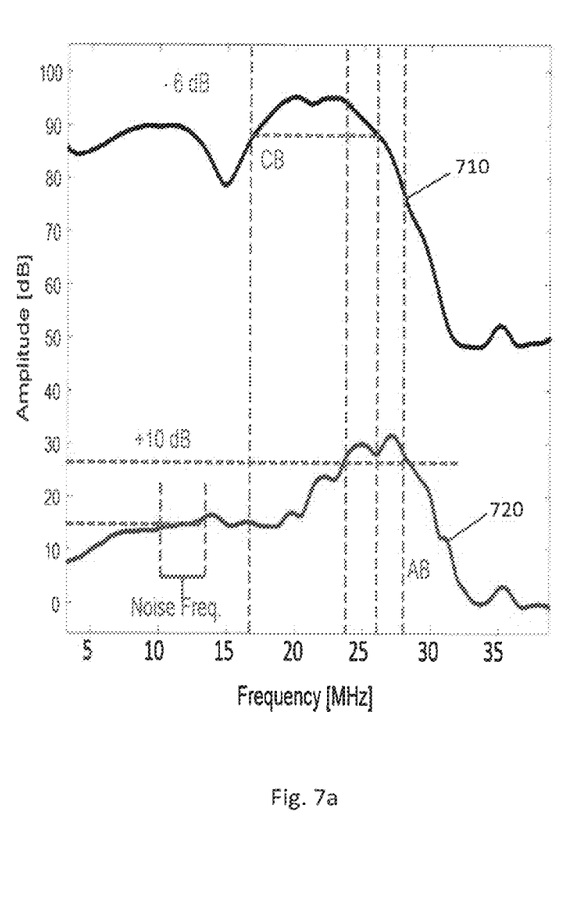
FIGS. 7a and 7b provide a graph showing an example of a spectrum from the deeper region of interest shown in FIG. 4b.
Figure 7B:
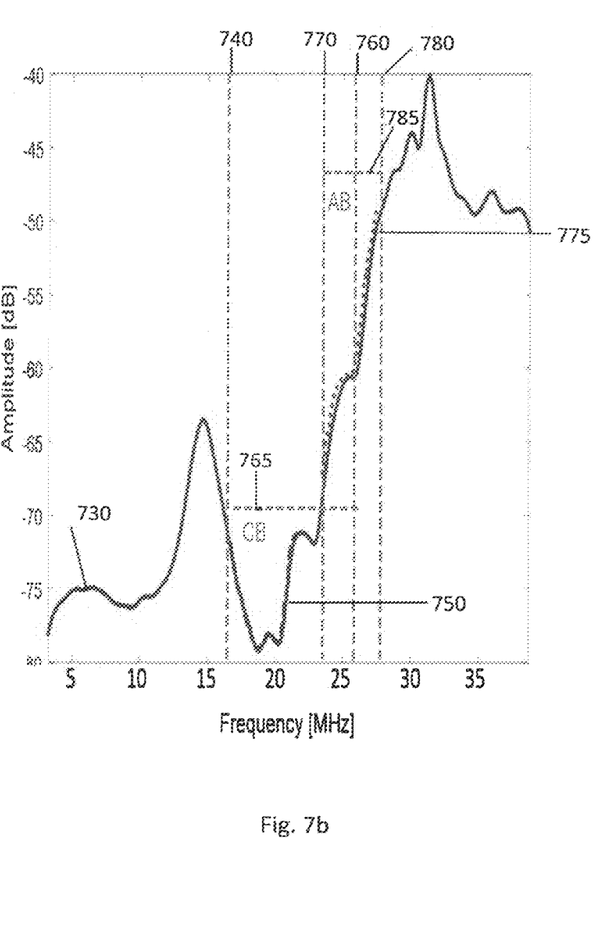

FIGS. 7a and 7b show spectra for signals from a deeper tissue area. The sample spectrum was computed for the deeper ROI 455 of FIG. 4b. FIGS. 7a and 7b show reference spectrum 710, signal spectrum 720 and difference spectrum 730. The amplitude of the reference spectrum as well as sample signal and spectrum are decreased for signals derived from the deeper ROI. Also the bandwidth of the sample signal is significantly reduced. FIG. 7b illustrates the conventional method of estimating the bandwidth between −6 dB points on the reference spectrum, with the gray dotted lines 740, 760, and 765. For comparison, the blue dotted lines of FIG. 7b, 770, 775, 780 and 785 illustrate the new adaptive-bandwidth method. Using the conventional method will include noise frequencies in the normalized power spectrum, red dotted line 750. This will cause erroneous QUS-parameter estimation. Using the adaptive-bandwidth method yields a narrower bandwidth for the spectrum of signals from the deeper ROI; however, the normalized power spectrum in that bandwidth is not corrupted by contributions from noise, green dotted line 775. In the noise-free portion of the normalized power spectrum, the normalized power spectrum shows a linear behavior with a positive slope. If the slope were estimated over the conventional bandwidth, the computed slope value would be much lower because of corruption of the spectrum by noise outside the noise-free bandwidth.

In the present examples, the spectral slope is referenced as a sample QUS parameter; however, several QUS parameters and scatterer properties can be estimated from the spectrum, and stable, reliable estimate values are best obtained using the broadest possible noise-free bandwidth, which is what the adaptive-bandwidth method of the present invention accomplishes.

Figure 8A:
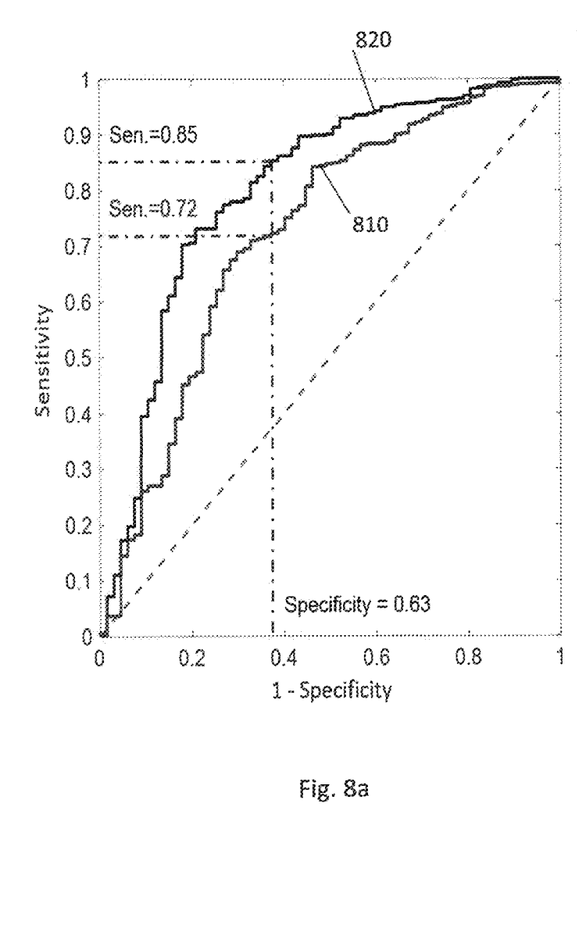
FIGS. 8a and 8b provide graphs showing an example of ROC results for adaptive bandwidth (black curves) versus conventional bandwidth methods (blue curves) and indicating superior classification performance when the adaptive-bandwidth method is applied.
Figure 8B:
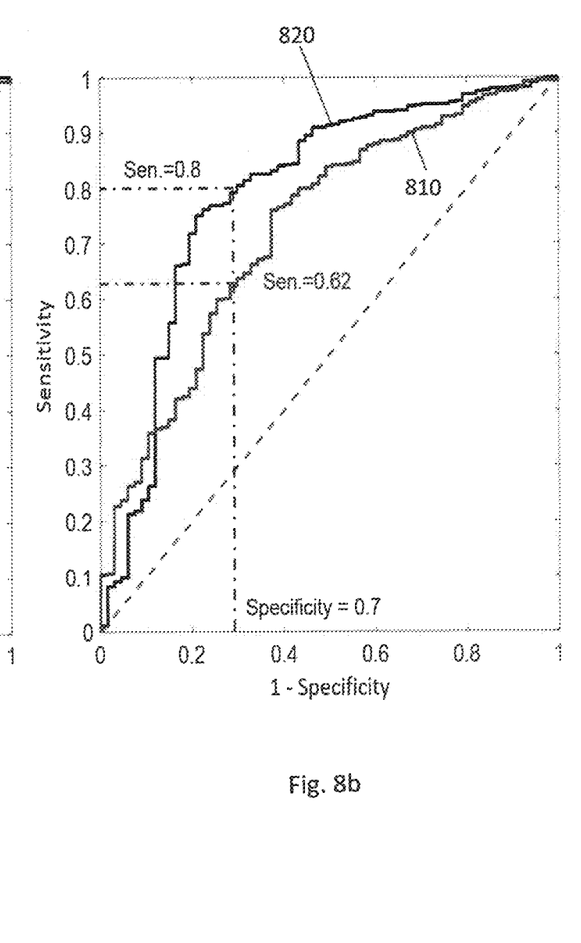

As illustrated by the relative-operating characteristics (ROC) results shown in FIGS. 8a and 8b for a prostate-cancer detection example, the adaptive-bandwidth method provides markedly superior performance to the conventional bandwidth method as shown by their ROC area-under-the-curve (AUC) values for prostate-cancer detection, by QUS. An AUC value of 1.0 indicates perfect classification and an AUC value of 0.5 indicates entirely random classification.

FIGS. 8a and 8b show ROC results for adaptive-bandwidth vs. conventional bandwidth methods when applied to detection of prostate cancer. FIG. 8a shows ROC values for adaptive-bandwidth, black line 820, and the conventional bandwidth method, blue line 810, for PSA combined with QUS estimates of effective scatter size (ESS) and effective acoustic concentration (EAC). The AUC for the adaptive band-width method is 0.8 (95% Confidence Interval (CI): 0.75:0.86) and is significantly greater than the AUC of 0.72 (CI: 0.64:0.80) for the conventional-bandwidth method. FIG. 8b shows the results for PSA combined with midband fit (Mf), Intercept (I0) and spectral slope (SS), wherein black line 820 represents the adaptive-bandwidth method and blue line 810 represents the conventional bandwidth method. The AUC for the adaptive-bandwidth method is 0.79 (CI: 0.72: 0.87) and for the conventional bandwidth method is 0.73 (CI: 0.69:0.77).

At the operating point with a specificity of 0.63 for a classifier trained based on PSA, ESC and ESS, the adaptive-bandwidth method achieved a 0.13 higher sensitivity compared to the conventional bandwidth method (as seen in FIGS. 8a and 8b).

Table 4, below, provides a summary of ROC analysis providing AUC for classifier trained with PSA, ESC, and ESS, (FIG. 8a) and trained with PSA, IO, Mf, and SS (See FIG. 8b) comparing the adaptive-bandwidth method with the conventional method. (SEN=Sensitivity, SPE=specificity and CI=confidence interval).

TABLE 4

| | QUS Parameter | AUC Adaptive Bandwidth (CI) | SEN at 63% SPE | AUC conventional Bandwidth (CI) | SEN at 70% SPE |
|---|---|---|---|---|---|
| FIG. 7a | PSA, ESC, ESS | 0.80 (0.75; 0.86) | 0.85 | 0.72 (0.64; 0.8) | 0.8 |
| FIG. 7b | PSA, I0, Mf, SS | 0.79 (0.72; 0.87) | 0.72 | 0.73 (0.69; 0.77) | 0.62 |

Although the present invention has been described in conjunction with specific embodiments, those of ordinary skill in the art will appreciate the modifications and variations that can be made without departing from the scope and the spirit of the present invention. Such modifications and variations are envisioned to be within the scope of the appended claims.

The invention claimed is:

1. A method for accurately determining properties of a biological material, comprising a patient's bodily tissue, in order to specifically identify where collection of cancer cells may be located in said biological material, comprising,
   performing an ultrasound scan of said biological material with ultrasound pulses, said biological material having a known depth;
   acquiring backscattered echo signals from said biological material being scanned with echo signal energy spanning a spectrum of frequencies and noise, wherein only including information useful to accurately determine said properties of said biological material in a specific bandwidth portion of said frequency spectrum;
   maximizing an adapted spectral bandwidth by selecting said specific bandwidth portion in said frequency spectrum to use in order to accurately determine said properties of said biological material, said specific bandwidth portion being adapted to be free of noise and compensate for degradation of signal amplitude by being narrow for echo signals coming from a relatively deep portion of said biological material and wider for echo signals coming from a less deep portion of said biological material;
   extracting information from signals included within said adapted spectral bandwidth, the information including normalized spectral parameter values, scatter-property estimates, and echo signal envelope statistics; and
   utilizing said extracted information to specifically identify where said collection of cancer cells may be located in said patient's bodily tissue.

2. The method in accordance with claim 1 further comprising noise level detection and identifying a frequency for the spectral content that is at least 10 dB above the noise level.

3. The method in accordance with claim 1 wherein said scatterer property estimates include effective scatter size and acoustic concentration based on spectral-parameter values.

4. The method in accordance with claim 1 wherein the extracted information further comprises generating additional parameter values of envelope statistics of said backscattered echo signals by using defined statistical models.

5. The method in accordance with claim 1 further comprising inputting said spectral parameter values, said scatterer property estimates, and said echo signal envelope statistics into a classifier.

6. The method in accordance with claim 1 further comprising assigning a classifier-score value to each of a plurality of variable values, wherein each of said classifier-score values for each variable-value combination indicates a relative likelihood of a specific material property.

7. A method in accordance with claim 1 wherein determining said properties of said patient's bodily tissue can include, but is not limited to, detecting a severity of ischemia, an extent of infection in the bodily tissue, a rate of healing in the bodily tissue, and a severity of burns to the bodily tissue.

8. A method for accurately determining properties of a non-biological material, comprising plastics or carbon fiber composites, in order to specifically identify where abnormalities may be located in said non-biological material, comprising;
   performing and ultrasound scan of said non-biological material with ultrasound pulses, said non-biological material having a known depth;
   acquiring backscattered echo signals from said non-biological material being scanned with echo signal energy spanning a spectrum of frequencies and noise, wherein only including information useful to accurately determine said properties of said non-biological material in a specific bandwidth portion of said frequency spectrum, maximizing an adapted spectral bandwidth by selecting said specific bandwidth portion in said frequency spectrum to use in order to accurately determine said properties of said non-biological material, said specific bandwidth portion being adapted to be free of noise and compensate for degradation of signal amplitude by being narrow for echo signals coming from a relatively deep portion of said non-biological material and wider for echo signals coming from a less deep portion of said non-biological material;

extracting information from signals included within said adapted spectral bandwidth, the information including normalized spectral parameter values, scatter-property estimates, and echo-signal envelope statistics; and utilizing said extracted information to specifically identify where abnormalities may be located in said non-biological material.

* * * * *